United States Patent [19]
Kinghorn et al.

[11] Patent Number: 6,099,495
[45] Date of Patent: Aug. 8, 2000

[54] IMPLANTABLE ELECTRICAL TRANSDUCER POWERED FROM CAPACITIVE STORAGE ENERGY SOURCE

[75] Inventors: Curtis D. Kinghorn, Lino Lakes; Charles R. Rogers, Maple Grove, both of Minn.

[73] Assignee: Medtronic, Inc., Minneapolis, Minn.

[21] Appl. No.: 09/070,255

[22] Filed: Apr. 30, 1998

[51] Int. Cl.⁷ .................................................. A61M 11/00
[52] U.S. Cl. .......................... 604/93; 604/67; 604/175; 604/890.1; 607/61
[58] Field of Search ...................... 607/61; 604/890.1, 604/93, 65–67, 131, 152, 246–249, 175; 128/DIG. 12, DIG. 13; 320/1, 2; 361/502, 504, 512, 525, 508

[56] References Cited

U.S. PATENT DOCUMENTS

| | | |
|---|---|---|
| 3,209,081 | 9/1965 | Ducote et al. . |
| 3,258,013 | 6/1966 | Druz . |
| 4,102,344 | 7/1978 | Conway et al. .......................... 128/419 |
| 4,221,219 | 9/1980 | Tucker ..................... 128/260 |
| 4,408,607 | 10/1983 | Maurer ..................... 128/419 |
| 4,408,608 | 10/1983 | Daly et al. ................. 128/421 |
| 4,443,218 | 4/1984 | DeCant, Jr. et al. ...................... 604/67 |
| 4,447,224 | 5/1984 | DeCant, Jr. et al. ...................... 604/67 |
| 4,496,343 | 1/1985 | Prosl et al. ................. 604/84 |
| 4,569,641 | 2/1986 | Falk et al. ............................. 417/417 |
| 4,692,147 | 9/1987 | Duggan ..................... 604/93 |
| 4,714,462 | 12/1987 | DiDomenico ............................ 604/67 |
| 4,838,887 | 6/1989 | Idriss ..................... 604/891 |
| 4,871,351 | 10/1989 | Feingold ..................... 604/66 |
| 4,931,050 | 6/1990 | Idriss ..................... 604/246 |
| 5,045,064 | 9/1991 | Idriss ..................... 604/132 |
| 5,049,141 | 9/1991 | Olive ..................... 604/891 |
| 5,061,242 | 10/1991 | Sampson ................. 604/118 |
| 5,067,943 | 11/1991 | Burke ..................... 604/141 |
| 5,088,983 | 2/1992 | Burke ..................... 604/141 |
| 5,207,666 | 5/1993 | Idriss et al. .............................. 604/891 |
| 5,312,439 | 5/1994 | Loeb ............................ 607/2 |
| 5,324,316 | 6/1994 | Schulman et al. ........................ 607/61 |
| 5,358,514 | 10/1994 | Schulman et al. ........................ 607/61 |
| 5,405,367 | 4/1995 | Schulam et al. .......................... 607/61 |
| 5,507,737 | 4/1996 | Palmskog ............................. 604/891.1 |
| 5,591,217 | 1/1997 | Barreras ..................... 607/61 |
| 5,820,589 | 10/1998 | Torgerson et al. ........................ 604/93 |

OTHER PUBLICATIONS

Fiandraa, "The First Pacemaker Impant In America," *Pacing and clinical Electrophysiology* vol. 11, No. 8, pp. 1117–1247, (Aug. 1988).

Capaciter Diviions, Matsushita Electronic Componests Co., Ltd, Panasonic Technical Guide of electriic Double Layer Capacitors.

van Lintel et all, "A Piezoelectric Micropump based on Mircromachining of Silicon," *Sensors and Actuatros*, 153–156,, (1988).

Smits, "Piezoelectric Micropump with Three Valves Working Peristaltically," A21–A23, *Sensors and Actuatros*, 203–206 (1990).

*Primary Examiner*—John D. Yasko
*Attorney, Agent, or Firm*—Banner & Witcoff, Ltd.

[57] ABSTRACT

An implantable system for treating a patient by an implantable electrical transducer and an implantable and rechargeable power source comprising a capacitive energy storage unit. A circuit is provided for recharging the power source without removing the power source from the patient. The power source preferably comprises a capacitor having a rating of at least 0.1 farads fabricated from carbonized phenol fibers.

15 Claims, 4 Drawing Sheets

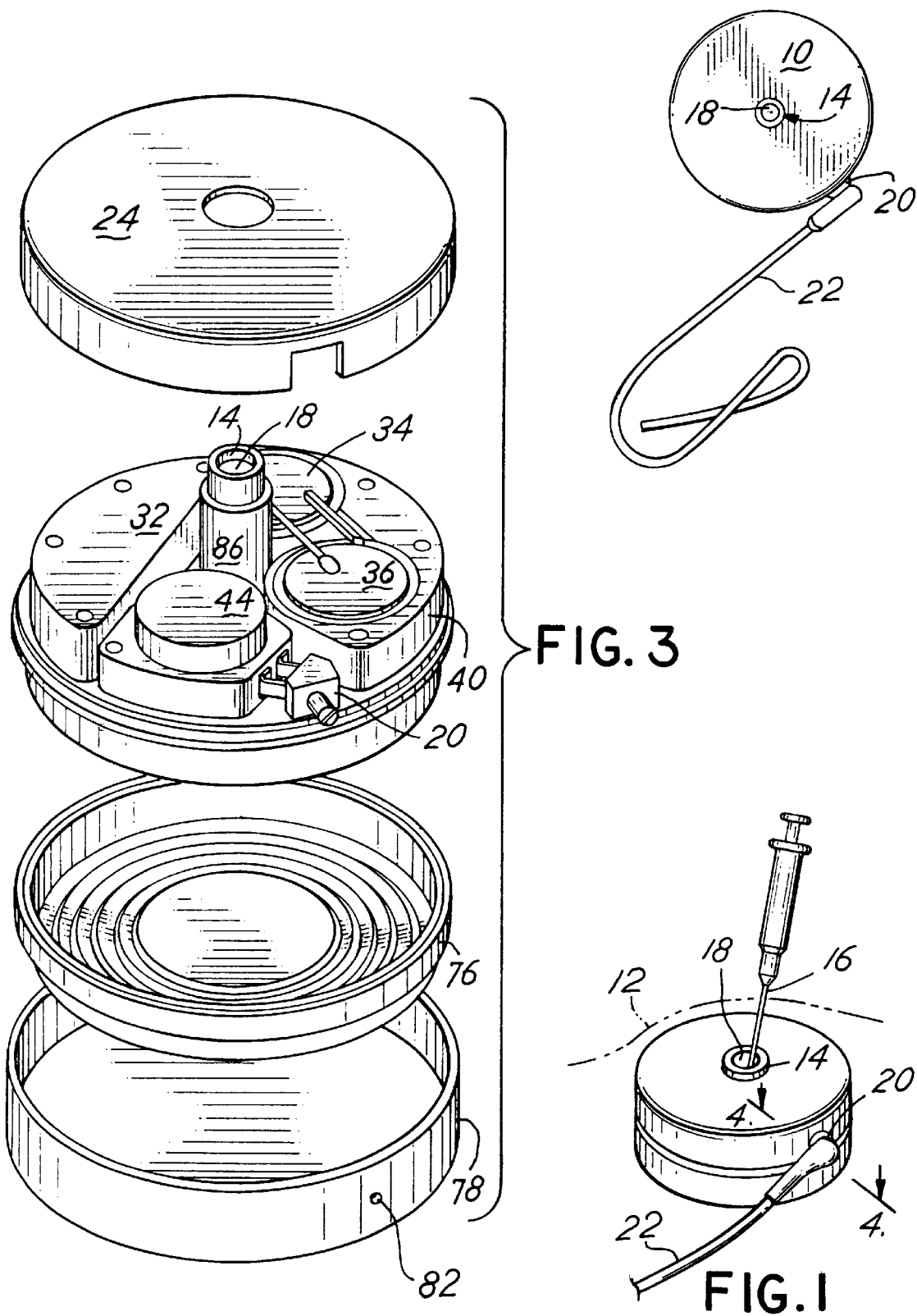

IMPLANTABLE ELECTRICAL TRANSDUCER POWERED FROM CAPACITIVE STORAGE ENERGY SOURCE

BACKGROUND OF THE INVENTION

1. Field of the Invention

This invention relates to medical devices and implantable techniques for treating patients by an implantable electrical transducer capable of movement, and more particularly to such techniques in which the transducer is powered by an implantable and rechargeable capacitive energy storage unit.

2. Description of the Related Art

Batteries have been used in the past to power implanted medical devices that include electrical transducers, such as motors that power pumps for infusing drugs and other medication. The batteries usually take the form of nickel cadmium batteries that typically are recharged via a radio frequency link. With such a system, it requires a significant time period, such as two hours, to recharge the batteries.

Capacitors have been used to a limited extent to power implantable devices in the past. For example, U.S. Pat. No. 4,408,607 (Maurer, issued Oct. 11, 1983) describes a capacitive energy source and circuitry for powering medical apparatus.

Other methods of powering implantable medical devices have also been tried. For example, U.S. Pat. No. 4,102,344 (Conway et al.) discloses an implantable device that is powered by an external high-frequency transmitter. U.S. Pat. No. 5,312,439 (Loeb) discloses an implantable device having an electrolytic capacitive storage electrode. U.S. Pat. No. 5,324,316 (Schulman et al.) discloses an implantable microstimulator which has one or more electrodes immersed in body fluids. The capacitor formed by the body fluids and the electrodes stores one hundred microcoulombs of charge. U.S. Pat. No. 5,358,514 (Schulman) discloses an implantable medical stimulator including a capacitor 20 without describing the capacitive rating or volumetric size of the capacitor. U.S. Pat. No. 5,405,367 (Schulman) discloses the use of a capacitor 20 on the order of 2–30 microfarads. U.S. Pat. No. 3,258,013 (Druz) discloses a defibrillator which is operable from a wholly self-contained battery power source 10. The Druz Patent also discloses shunt condensers or capacitors 36 and 37 which are part of a two-sectioned lumped constant delay line. A delay line discharge pulsing circuit is employed as an energy storage device. Capacitors 36 and 37 are 20 microfarads each. U.S. Pat. No. 3,209,081 (Ducote) discloses an implant with transistors powered from a radio receiver. Voltage is applied to a capacitor 20 as long as the power transmitter is functioning. U.S. Pat. No. 4,408,608 (Daly) discloses an implantable stimulator using a capacitor C1 that tunes a coil L1. U.S. Pat. No. 5,591,217 (Barreras issued Jan. 7, 1997) discloses an implantable stimulator with a capacitive power source having a capacitive rating of at least 0.1 farads or higher.

Although the foregoing techniques have recognized some value in the use of capacitors in medical devices, they either have used conventional capacitors which are inferior to nickel cadmium batteries in significant respects, have limited application of capacitive power sources to electrical stimulation.

SUMMARY OF THE INVENTION

The inventors have surprisingly discovered that a rechargeable capacitive energy storage unit can be implanted in a patient and can be used to power an implantable electrical transducer capable of moving from one position to another for providing treatment for the patient. Such a transducer may take the form of a stepping motor used to drive a pump that delivers drugs or other medication internally to specific tissue within the patient.

In such an environment, the implantable electrical transducer may be responsive to electrical power provided by the storage unit. An implantable and rechargeable power source is provided for the transducer. Means are also provided for recharging the power source within a predetermined recharge time period without removing the power source from the patient. As a result, the patient can be treated by movement of the transducer while minimizing the time required for recharging of the power source. This technique results in improved reliability and convenience to the patient.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 1 is a diagrammatic view of a preferred form of device made in accordance with the present invention implanted beneath the skin (shown in phantom) with a reservoir of the device being filled by a hypodermic syringe;

FIG. 2 is a plan view of the device shown in FIG. 1;

FIG. 3 is a exploded view of the device shown in FIG. 1 with the catheter removed;

DESCRIPTION OF THE PREFERRED EMBODIMENTS

Figure 4:
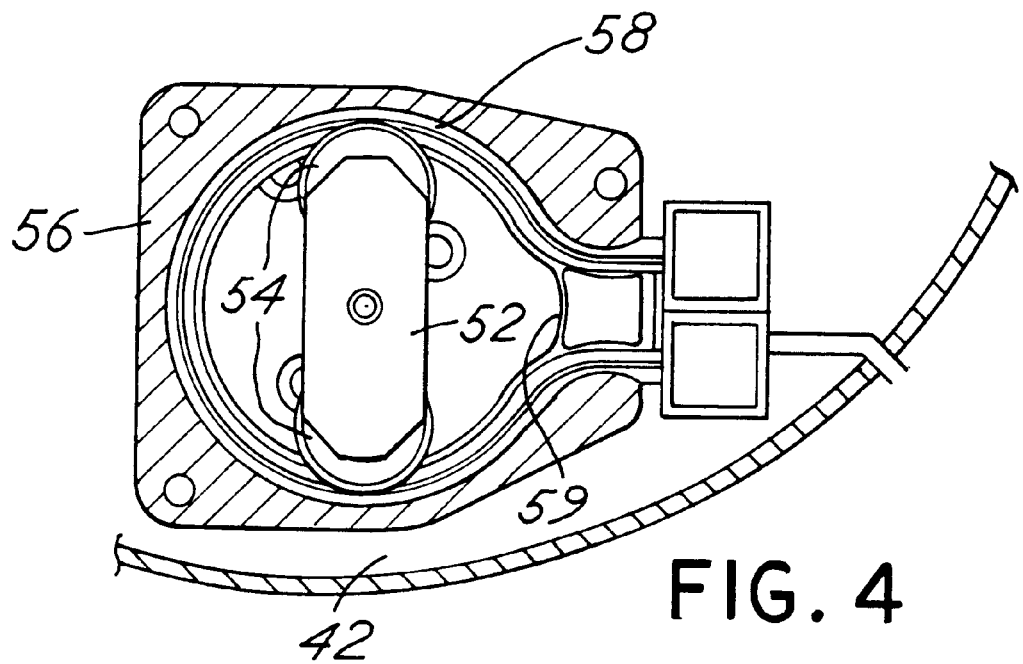
FIG. 4 is a cross-sectional view of the pump/meter of the device taken along line 4—4 of FIG. 1.

Referring to FIGS. 1 and 2, an administration system or device 10 made in accordance with a preferred embodiment is shown implanted below a layer of skin 12 indicated in phantom. The administration device has a port 14 into which a hypodermic needle 16 can be inserted through the skin 12 to insert a quantity of a liquid agent, such as a medication, a growth factor, an antisense agent, an ionic solution, one or more antibodies, a hormone, proteins or peptides, viruses, cell suspension, a chemotherapeutic agent or toxin, or some drug, through a septum (not shown) into a drug reservoir (not shown) located within drug administration device 10. The liquid agent is delivered from device 10 through a catheter port 20 to which a catheter 22 is attached. The catheter 22 is positioned to deliver the agent to spaced infusion sites.

Referring to FIG. 3, a circuit module 32 is driven by suitable capacitive energy storage units 34 and 36 which are connected to input terminals of the circuit module 32. Circuit module 32 provides instruction a peristaltic roller pump 44 for delivery of the liquid agent. Pump 44 is connected to a catheter port 20 which provides an outlet conduit (not shown) of catheter 22 screwed onto port 20.

Pump 44 receives its input from an inlet conduit (not shown) which may be from a fluid reservoir within device 10. The peristaltic roller pump 44 is shown in further detail in FIGS. 4 and 5. A motor 46 drives a gear train 48, which in turn drives a shaft 50 that is connected to an arm 52. As preferred, motor 46 is a two pole subminiature stepping motor of the type used in digital watches having analog time indicating means. The winding of motor 46 is driven by electrical pulses from circuit module 32 which steps the motor 46 through a fixed arc for each electrical pulse. Other embodiments may involve other types of motors and other methods for driving the motor.

Rollers 54 are each mounted for rotation about their axes at both ends of arm 52 which is rotatable through 360°. As shaft 50 is rotated, arm 52 and rollers 54 are rotated about the axis of shaft 50. Arm 52 is located within a housing 56 and a flexible tube 58 lines the interior wall of housing 56 as shown in FIG. 4. A shim 59 is interposed between rollers 54 and tubing 58 to aid in balancing the forces applied to shaft 50 as rollers 54 traverse a complete revolution of shaft 50. As shaft 50 rotates, the wheels 54 roll along shim 59 and compress tubing 58 against the inner wall of housing 56.

Alternative embodiments of pump 44 may include those disclosed in U.S. Pat. No. 4,692,147 (Duggan, issued Sep. 8,1987) or those described by B. T. G. van Lintel et al. in "A Piezoelectric Micropump Based on Micromachining of Silicon," 15 *Sensors and Actuators* 153–156 (1988) and by Jan G. Smits in "Piezoelectric Micropump with Three Valves Working Peristaltically," A21–A23 *Sensors and Actuators* 203–206 (1990). Those skilled in the art will appreciate that other pump embodiments are also conceivable.

Figure 6:
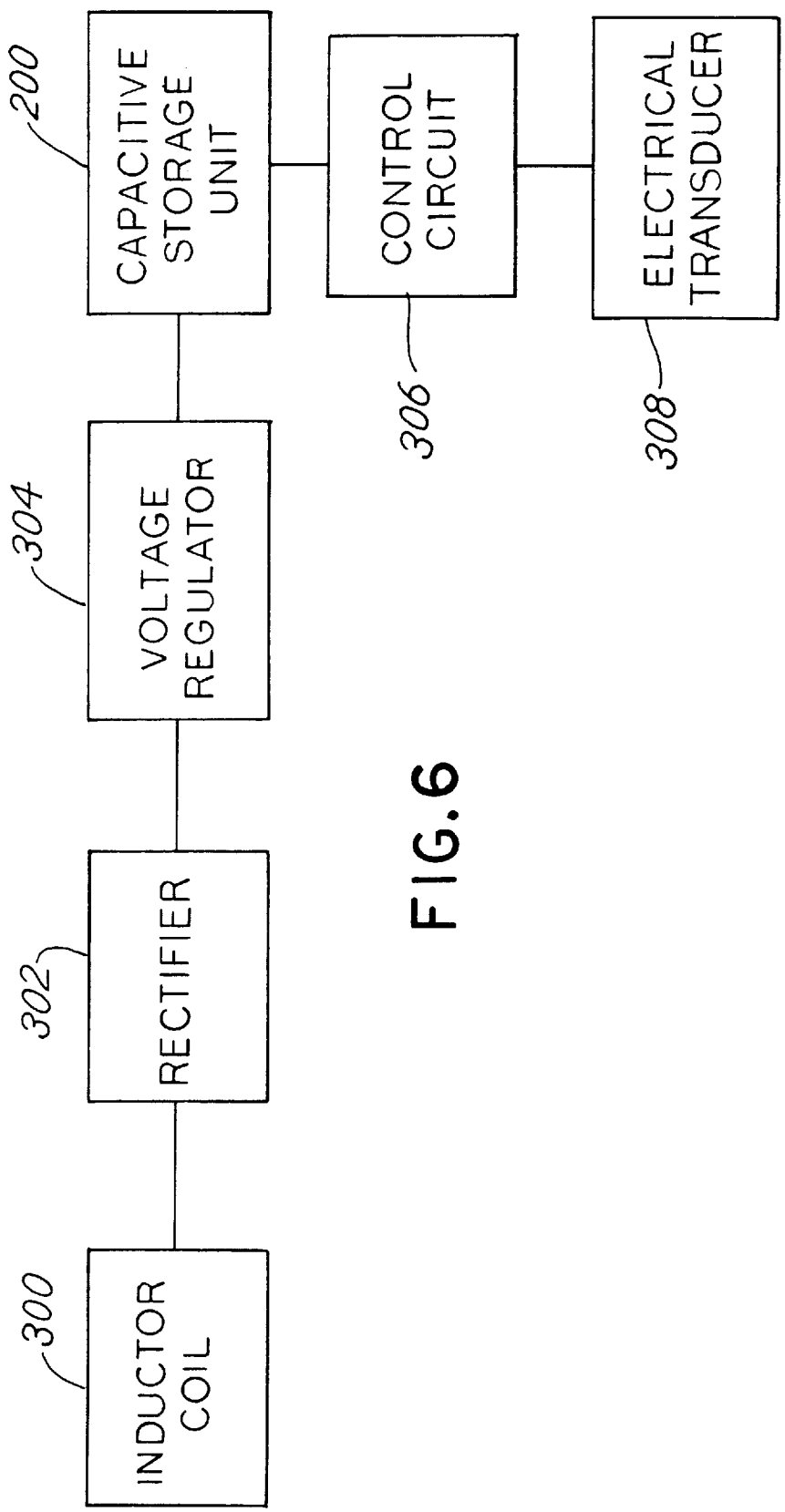
FIG. 6 is an electrical schematic block diagram of a preferred form of charging unit for the capacitive power source shown in FIG. 3.
Figure 7:
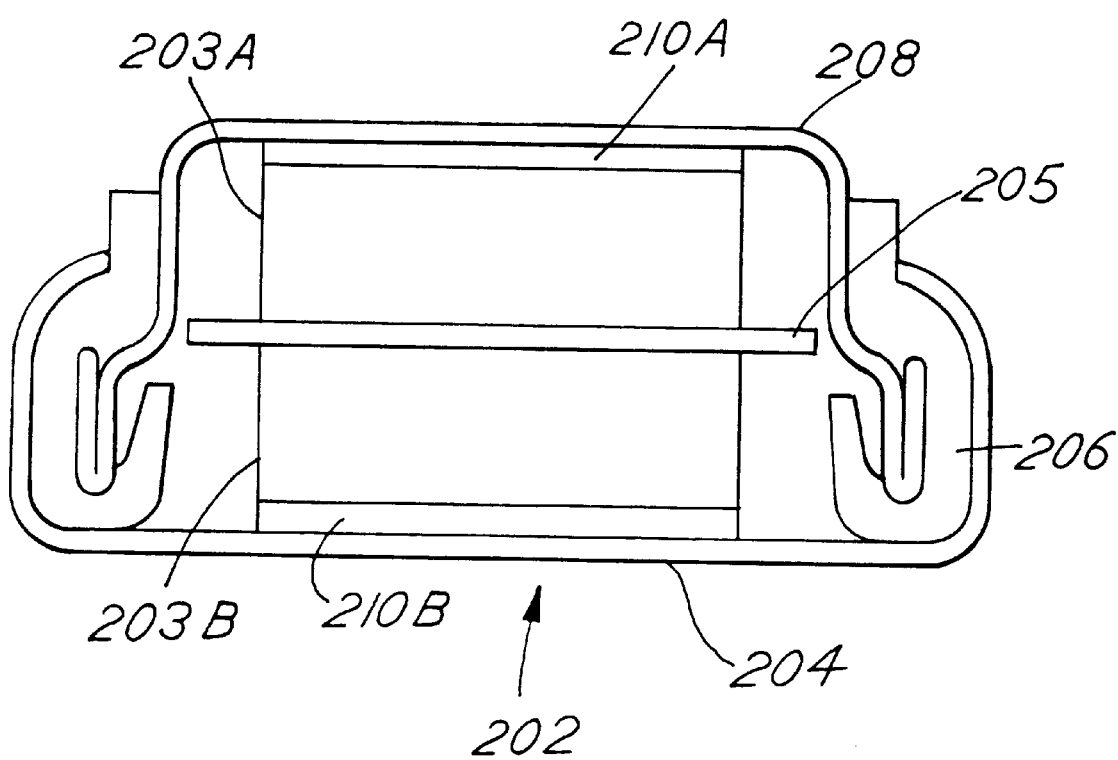
FIG. 7 is a cross-sectional view of a preferred form of capacitive energy storage unit made in accordance with the present invention.

Capacitive storage cells 34 and 36 are collectively referred to as capacitive storage unit 200 in FIG. 6. Each capacitive storage cell 34 or 36 which may include one or more of identical cells such as cell 202 shown in FIG. 7. Cell 202 is preferably electric double layer capacitors. Electrodes 203A and 203B within cell 202 are an activated carbon fiber made from activated carbonized phenol fibers. Sides 210A and 210B of electrodes 203A and 203B are flame spray coated with aluminum. Electrodes 203A and 203B are welded to bottom case 204 and top cover 208 and function as the current collector. Electrodes 203A and 203B are then impregnated with a liquid electrolyte. A separator 205 with high insulating properties against ion penetration is positioned between both electrodes 203A and 203B to prevent short circuiting. Sealing is completed by adding packing 206 between a top cover 208 and bottom case 204.

Negative and positive electric charges form on the boundary between the solid activated carbon fibers of electrodes 203A and 203B and the liquid electrolyte. The boundary area between these charges is the electric double layer. The area increases as higher voltages are applied which increases the charge. The electric double layer acts as an insulator/dielectric and does not allow current flow when an external DC voltage is applied. However, as the voltage is increased, an avalanche point is reached and current will begin to flow. The magnitude of this voltage is the "decomposition voltage". Further increasing this voltage will cause the electrolyte to decompose causing additional current flow. The withstand voltage rating of cell 202 is determined by the decomposition voltage.

Cell 202 preferably has a capacitance range of 0.1–1.0 farads and a voltage rating of about 5.5 volts DC. Cell 202 of the type described can be implemented by type SG or ST capacitors sold by Matsushita Electronic Components Company, Ltd. under the trade name "Panasonic". Storage unit 200 may thereby be fabricated with a smaller volume than ordinary capacitors.

Figure 5:
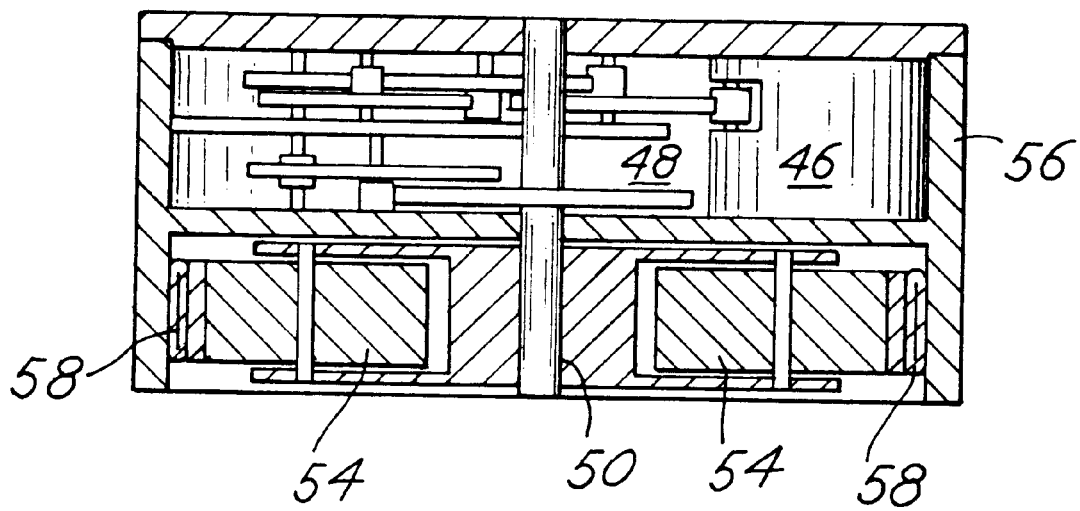
FIG. 5 is a cross-sectional view of the pump shown in FIG. 4.

Referring to FIG. 6, a preferred form of implantable circuitry for recharging unit 200 basically comprises an inductor coil 300, a rectifier 302, and a voltage regulator 304 connected as shown. Details of such circuitry suitable for an implanted medical device are described in the above-identified U.S. Pat. No. 5,591,217 (Barreras, issued Jan. 7, 1997). Alternatively, the capacitive storage unit 200 may be recharged by an implantable power supply as shown, for example, in U.S. Pat. No. 4,408,607 (Maurer, issued Oct. 11, 1983). Storage unit 200 is used to supply electrical power to a conventional control circuit 306 which may be implemented by circuit module 32 of FIG. 3. Circuit module 32 may be used to drive a variety of electrical transducers 308, such as stepping motor 46 (FIG. 5).

In alternative embodiments, storage unit 200 powers any number of other types of pumping means and transducing means. Transducing means may include any number of actuators or motors including, for example, a stepper motor, an AC motor, a DC motor, an electrostatic diaphragm, an electrostatic motor, a piezoelectric diaphragm, a piezoelectric motor, a solenoid, or a Nitonol shape memory alloy. Pumping means may include, for example, a peristaltic pump, a diaphragm, a piston, a valve, a valved accumulator, a proportional valve, a bistable valve, and a rupturable membrain. Such devices may be those disclosed in U.S. Patent Nos. 5,207,666; 5,088,983; 5,067,943; 5,061,242; 5,049,141; 5,045,064; 4,931,050; 4,838,887; 4,714,462; 4,496,343; 4,447,224; 4,443,218; 4,221,219; 4,569,641.

Capacitive storage unit 200 may be used to power pump 44 for approximately at least 8 hours and possibly much longer. After the charge is somewhat depleted, recharging is accomplished by the use of a radio frequency antennae system that provides electromagnetic waves that induce a voltage in inductor coil 300 (FIG. 6). Inductor coil 300 generates a fluctuating power signal from the electromagnetic energy received from the transmitting system located outside the patient. Inductor coil 300 generates a fluctuating power signal from the received electromagnetic energy. The power signal is rectified by rectifier 302 and is used to operate a conventional voltage regulator 304 that provides charge to capacitive storage unit 200 up to a predetermined rated voltage. Depending upon the recharging apparatus, the recharge time may require as little as ten minutes or less. This is an important feature because the previously used nickel cadmium batteries required approximately two hours to recharge. The electromagnetic energy received by inductor coil 300 may have a frequency in the radio frequency range and preferable may have a frequency in the range of about 8 kHz. Capacitive storage unit 200 may be used to power all of the electrical apparatus required in order to operate the transducer, such as a microprocessor (not shown) and other related electronics.

Those skilled in the art will recognize that the preferred embodiments may be altered or amended without departing from the true spirit and scope of the invention, as defined in the accompanying claims.

We claim:

1. An implantable medical system for treating a patient comprising in combination:

an implantable electrical transducer responsive to electrical power and capable of moving from a first position to a second position for providing treatment for said patient;

an implantable and rechargeable power source for said transducer, said power source comprising a capacitive energy storage unit for supplying said electrical power; and means for recharging said power source within a predetermined recharge time period without removing said power source from said patient, whereby said patient can be treated by movement of said transducer while minimizing the time required for recharging of said power source.

2. A system, as claimed in claim 1, wherein said transducer comprises a transducing means.

3. A system, as claimed in claim 2, wherein said transducing means is selected from the group consisting of a stepper motor, an AC motor, a DC motor, an electrostatic diaphragm, an electrostatic motor, a piezoelectric diaphragm, a piezoelectric motor, a solenoid, or a Nitonol shape memory alloy.

4. A system, as claimed in claim 2, wherein said transducer further comprises a pumping means.

5. A system, as claimed in claim 4, wherein said pumping means is selected from the group consisting of a peristaltic pump, a diaphragm, a piston, a valve, a valved accumulator, a proportional valve, a bistable valve, a rupturable membrain.

6. A system, as claimed in claim 1, wherein said storage unit comprises a capacitor having a capacitive rating of at least 0.1 farads and an energy storage capacity sufficient to supply said electrical power for at least 8 hours.

7. A system, as claimed in claim 1, wherein said recharge time period is 10 minutes or less.

8. A system, as claimed in claim 1, wherein said storage unit comprises a double layer capacitor.

9. A system, as claimed in claim 1, wherein said capacitor is fabricated from carbonized phenol fibers.

10. A system, as claimed in claim 1, wherein said means for recharging said power source comprises an inductor coil for generating a fluctuating power signal from electromagnetic energy.

11. A system, as claimed in claim 10 wherein said means for recharging said power source further comprises a rectifier for generating a direct current power signal in response to said fluctuating power signal.

12. A system, as claimed in claim 11, wherein said means for recharging said power source further comprises a voltage regulator for providing charge to said storage unit up to a predetermined rated voltage.

13. A system, as claimed in claim 10, wherein said electromagnetic energy has a frequency in the range of radio frequency wave.

14. A system, as claimed in claim 10, wherein said electromagnetic energy has a frequency in the range of about 8 kHz.

15. A system, as claimed by in claim 1, further comprising a control circuit coupled to said capacitive energy storage unit for driving said transducer.

* * * * *